(12) United States Patent
Wang et al.

(10) Patent No.: US 12,329,441 B2
(45) Date of Patent: Jun. 17, 2025

(54) TWO-STAGE ELECTROSURGICAL DEVICE FOR VESSEL SEALING

(71) Applicant: GYRUS ACMI, INC., Westborough, MA (US)

(72) Inventors: Huisun Wang, Maple Grove, MN (US); Kester Julian Batchelor, Mound, MN (US); Zane R. Ward, Minneapolis, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 971 days.

(21) Appl. No.: 17/306,000

(22) Filed: Jul. 19, 2021

(65) Prior Publication Data

US 2021/0338314 A1 Nov. 4, 2021

Related U.S. Application Data

(63) Continuation of application No. 15/602,601, filed on May 23, 2017, now Pat. No. 11,076,908.
(Continued)

(51) Int. Cl.
*A61B 18/14* (2006.01)
*A61B 17/28* (2006.01)
(Continued)

(52) U.S. Cl.
CPC .. *A61B 18/1445* (2013.01); *A61B 2017/2825* (2013.01); *A61B 2017/2926* (2013.01);
(Continued)

(58) Field of Classification Search
CPC ........ A61B 18/1445; A61B 2017/2825; A61B 2018/00589; A61B 2018/00595;
(Continued)

(56) References Cited

U.S. PATENT DOCUMENTS 3,503,396 A 3/1970 Pierie et al.
5,693,051 A 12/1997 Schulze et al.
(Continued)

FOREIGN PATENT DOCUMENTS

CA 2541039 A1 9/2006
CN 101969874 A 2/2011
(Continued)

OTHER PUBLICATIONS

"European Application Serial No. 17174083.0, Communication Pursuant to Article 94(3) EPC mailed Sep. 15, 2021", 3 pgs.
(Continued)

*Primary Examiner* — Sean W Collins
(74) *Attorney, Agent, or Firm* — Schwegman Lundberg & Woessner, P.A.

(57) ABSTRACT

A forceps includes an end effector assembly with a first jaw having a tissue sealing surface and an electrode on the sealing surface, and a second jaw having a tissue sealing surface and an electrode on the sealing surface. The first jaw and the second jaw move between an open position and a closed position. The sealing surface of at least one of the first jaw and the second jaw has a flexible medial section and rigid lateral sections.

17 Claims, 10 Drawing Sheets

Related U.S. Application Data (60) Provisional application No. 62/344,749, filed on Jun. 2, 2016, provisional application No. 62/407,732, filed on Oct. 13, 2016.

(51) Int. Cl.
 *A61B 17/29* (2006.01)
 *A61B 18/00* (2006.01)
 *A61B 18/12* (2006.01)

(52) U.S. Cl.
 CPC .............. *A61B 2018/00345* (2013.01); *A61B 2018/00589* (2013.01); *A61B 2018/00595* (2013.01); *A61B 2018/00601* (2013.01); *A61B 2018/00607* (2013.01); *A61B 2018/0063* (2013.01); *A61B 18/12* (2013.01); *A61B 2018/126* (2013.01); *A61B 2018/1455* (2013.01); *A61B 2018/1457* (2013.01)

(58) Field of Classification Search
 CPC A61B 2018/00601; A61B 2018/00607; A61B 2018/0063; A61B 2018/126; A61B 2018/1455
 See application file for complete search history.

(56) References Cited

U.S. PATENT DOCUMENTS

| | | | |
|---|---|---|---|
| 5,728,121 | A | 3/1998 | Bimbo et al. |
| 5,752,973 | A | 5/1998 | Kieturakis |
| 5,754,928 | A | 5/1998 | Moe et al. |
| 6,086,586 | A | 7/2000 | Hooven |
| 6,113,598 | A | 9/2000 | Baker |
| 6,123,701 | A | 9/2000 | Nezhat |
| 6,406,485 | B1 | 6/2002 | Hossain et al. |
| 6,926,716 | B2 | 8/2005 | Baker et al. |
| 6,942,676 | B2 | 9/2005 | Buelna |
| 7,041,102 | B2 | 5/2006 | Truckai et al. |
| 7,182,775 | B2 | 2/2007 | De Guillebon et al. |
| 7,276,068 | B2 | 10/2007 | Johnson et al. |
| 7,491,202 | B2 | 2/2009 | Odom et al. |
| 7,632,269 | B2 | 12/2009 | Truckai et al. |
| 8,192,433 | B2 | 6/2012 | Johnson et al. |
| 8,262,655 | B2 | 9/2012 | Ghabrial et al. |
| 8,298,232 | B2 | 10/2012 | Unger |
| 8,317,787 | B2 | 11/2012 | Hanna |
| 8,382,754 | B2 | 2/2013 | Odom et al. |
| 8,556,929 | B2 | 10/2013 | Harper et al. |
| 8,597,297 | B2 | 12/2013 | Couture et al. |
| 8,647,343 | B2 | 2/2014 | Chojin et al. |
| 8,795,274 | B2 | 8/2014 | Hanna |
| 8,945,125 | B2 | 2/2015 | Schechter et al. |
| 8,968,308 | B2 | 3/2015 | Horner et al. |
| 11,076,908 | B2 | 8/2021 | Wang et al. |
| 2004/0143263 | A1 | 7/2004 | Schechter et al. |
| 2005/0203507 | A1 | 9/2005 | Truckai et al. |
| 2007/0213711 | A1 | 9/2007 | Eder et al. |
| 2008/0091189 | A1 | 4/2008 | Carlton |
| 2009/0054894 | A1 | 2/2009 | Yachi |
| 2009/0131933 | A1* | 5/2009 | Ghabrial ............ A61B 18/1445 606/51 |
| 2009/0131934 | A1* | 5/2009 | Odom ................ A61B 18/1445 606/51 |
| 2009/0149853 | A1 | 6/2009 | Shields et al. |
| 2009/0182333 | A1* | 7/2009 | Eder .................. A61B 18/1442 606/51 |
| 2010/0057083 | A1 | 3/2010 | Hanna |
| 2010/0057084 | A1* | 3/2010 | Hanna ................ A61B 18/1445 606/51 |
| 2011/0118736 | A1 | 5/2011 | Harper et al. |
| 2011/0278343 | A1 | 11/2011 | Knodel et al. |
| 2011/0319886 | A1 | 12/2011 | Chojin et al. |
| 2013/0014375 | A1 | 1/2013 | Hempstead et al. |
| 2013/0046303 | A1* | 2/2013 | Evans ................ A61B 18/1445 606/45 |
| 2014/0276731 | A1* | 9/2014 | Voegele ................ A61B 18/18 606/33 |
| 2015/0250528 | A1 | 9/2015 | Walberg et al. |
| 2015/0305796 | A1 | 10/2015 | Wang |
| 2016/0066980 | A1 | 3/2016 | Schall et al. |
| 2017/0042604 | A1 | 2/2017 | Mcfarland et al. |
| 2017/0348043 | A1 | 12/2017 | Wang et al. |

FOREIGN PATENT DOCUMENTS

| | | |
|---|---|---|
| CN | 102119010 A | 7/2011 |
| CN | 102160817 A | 8/2011 |
| CN | 102727283 A | 10/2012 |
| CN | 105073036 A | 11/2015 |
| CN | 107456270 A | 12/2017 |
| CN | 107456270 B | 8/2021 |
| CN | 113768613 A | 12/2021 |
| EP | 2353534 A1 | 8/2011 |
| EP | 2554135 A1 | 2/2013 |
| EP | 3251624 A2 | 12/2017 |
| EP | 3251624 B1 | 9/2022 |

OTHER PUBLICATIONS

"European Application Serial No. 17174083.0, Response filed Dec. 23, 2021 to Communication Pursuant to Article 94(3) EPC mailed Sep. 15, 2021", 73 pgs.

"U.S. Appl. No. 15/602,601, 312 Amendment filed Jun. 29, 2021", 7 pgs.

"U.S. Appl. No. 15/602,601, Advisory Action mailed Jul. 27, 2020", 4 pgs.

"U.S. Appl. No. 15/602,601, Examiner Interview Summary mailed Feb. 19, 2020", 3 pgs.

"U.S. Appl. No. 15/602,601, Final Office Action mailed Mar. 5, 2020", 13 pgs.

"U.S. Appl. No. 15/602,601, Non Final Office Action mailed Nov. 18, 2019", 12 pgs.

"U.S. Appl. No. 15/602,601, Non Final Office Action mailed Nov. 24, 2020", 13 pgs.

"U.S. Appl. No. 15/602,601, Notice of Allowance mailed Mar. 31, 2021", 11 pgs.

"U.S. Appl. No. 15/602,601, PTO Response to Rule 312 Communication mailed Jul. 9, 2021", 2 pgs.

"U.S. Appl. No. 15/602,601, Response filed Feb. 18, 2020 to Non Final Office Action mailed Nov. 18, 2019", 21 pgs.

"U.S. Appl. No. 15/602,601, Response filed Feb. 24, 2021 to Non Final Office Action mailed Nov. 24, 2020", 13 pgs.

"U.S. Appl. No. 15/602,601, Response filed Jul. 6, 2020 to Final Office Action mailed Mar. 5, 2020", 17 pgs.

"U.S. Appl. No. 15/602,601, Response filed Oct. 23, 2019 to Restriction Requirement mailed Sep. 12, 2019", 9 pgs.

"U.S. Appl. No. 15/602,601, Restriction Requirement mailed Sep. 12, 2019", 9 pgs.

"Chinese Application Serial No. 201710409426.6, Office Action mailed Mar. 20, 2020", W/English Translation, 22 pgs.

"Chinese Application Serial No. 201710409426.6, Office Action mailed Jul. 3, 2019", W/English Translation, 16 pgs.

"Chinese Application Serial No. 201710409426.6, Office Action mailed Dec. 8, 2020", with English translation, 22 pgs.

"Chinese Application Serial No. 201710409426.6, Response filed Feb. 21, 2021 to Office Action mailed Dec. 8, 2020", w/English Claims, 10 pgs.

"Chinese Application Serial No. 201710409426.6, Response filed May 14, 2021 to Examiner Telephone Interview", with machine translation, 12 pgs.

"Chinese Application Serial No. 201710409426.6, Response filed Aug. 3, 2020 to Office Action mailed Mar. 20, 2020", with machine translation, 8 pgs.

"European Application Serial No. 17174083.0, Extended European Search Report mailed Feb. 27, 2018", 9 pgs.

(56) References Cited

OTHER PUBLICATIONS

"European Application Serial No. 17174083.0, Partial European Search Report mailed Oct. 24, 2017", 10 pgs.
"European Application Serial No. 17174083.0, Response filed Sep. 26, 2018 to Extended European Search Report mailed Feb. 27, 2018", 18 pgs.
Paul, Palinski J, et al., "CoPending PCT Pending Application PCT/US2016/012823 filed Jan. 11, 2016".
"Chinese Application Serial No. 202110929252.2, Office Action mailed Jan. 12, 2024", W/English Translation, 11 pgs.
"Chinese Application Serial No. 202110929252.2, Office Action mailed Aug. 6, 2024", w/ English translation, 15 pgs.
"Chinese Application Serial No. 202110929252.2, Response filed May 23, 2024 to Office Action mailed Jan. 12, 2024", w/ english claims, 15 pgs.

\* cited by examiner

TWO-STAGE ELECTROSURGICAL DEVICE FOR VESSEL SEALING

RELATED APPLICATIONS

This application is a Continuation of U.S. patent application Ser. No. 15/602,601 filed May 23, 2017 and issued on Aug. 3, 2021 as U.S. Pat. No. 11,076,908, which claims the benefit of U.S. Provisional Patent Application No. 62/344,749, filed on Jun. 2, 2016, and U.S. Provisional Patent Application No. 62/407,732, filed on Oct. 13, 2016.

The contents of the above applications are incorporated herein by reference in their entirety.

FIELD

The present disclosure relates to an electrosurgical device. More specifically, the present disclosure relates to an electrosurgical device for vessel sealing.

BACKGROUND

The statements in this section merely provide background information related to the present disclosure and may not constitute prior art.

Generally forceps may be utilized for laparoscopic surgery. The forceps may be employed to control delicate movements inside a patient and may include a gripping assembly or a cutting assembly. Further, the forceps may utilize electrical energy in the gripping assembly. Typically, the forceps have a pair of opposed resilient jaws that are closed against each other by pulling the jaws into a distal end of a shaft that captures a portion of the jaws that is wider than the distal end opening of the shaft so that the jaws are moved together. Similarly the shaft may be pushed over the jaws so that the jaws are moved together to create a gripping force. In both of these arrangements, the shaft captures the jaws and acts as a cam that forces the jaws together to create the gripping force.

Current bipolar electrosurgical sealing forceps employ a pair of jaws with RF energy to coagulate a vessel and further employ a moveable cutting blade to cut the sealed vessel after coagulation. Such devices, however, require a high jaw force to compress the vessel tissue for desired sealing results. The high jaw force can cause unwanted tissue damage, since, for example, the jaw force requirements for large vessels and small vessels are different.

Accordingly, there is a need in the art for electrosurgical forceps that can seal both large and small vessels.

SUMMARY

The present disclosure provides an end effector assembly with a two-stage configuration that optimally seals both small and large vessels.

Accordingly, pursuant to one aspect of the present invention, a forceps includes an end effector assembly with a first jaw having a tissue sealing surface and an electrode on the sealing surface, and a second jaw having a tissue sealing surface and an electrode on the sealing surface. The first jaw and the second jaw move between an open position and a closed position. The sealing surface of at least one of the first jaw and the second jaw has a flexible medial section and rigid lateral sections.

The foregoing aspect of the present invention can be further characterized by one or any combination of the features described herein, such as: the sealing surfaces of both the first jaw and the second jaw have a flexible medial section and rigid lateral sections; each of the first jaw and the second jaw includes a jaw body and a sealing plate, the exterior surface of the sealing plate being the sealing surface of each of the first jaw and the second jaw, and wherein the jaw body of at least one of the first jaw and the second jaw includes a support member, and wherein a layer of pliable material is disposed between the support member and the sealing plate, the layer of pliable material being made of separate cells placed side by side with different stiffnesses, the center cells being more flexible than the lateral cells; the medial section is proud of the lateral sections when the first jaw and the second jaw are in the open position; the medial section is raised from the lateral sections with a spring member; the medial section is electrically connected to a generator and a selective electrical contact electrically connects the lateral sections to the medial section when the first jaw and the second jaw move to the closed position; the medial section is electrically connected to a generator and a selective electrical contact electrically connects the lateral sections to the medial section when the first jaw and the second jaw move to the closed position; and the end effector assembly includes a slot extending axially through a substantial portion of the first jaw and the second jaw and further includes a blade that translates within the slot.

Accordingly, pursuant to another aspect of the present invention, a method of using forceps includes one or more of the following steps: opening a first jaw and a second jaw of the forceps, the first jaw having a tissue sealing surface and an electrode on the sealing surface and the second jaw having a tissue sealing surface and an electrode on the sealing surface, the sealing surface of at least one of the first jaw and the second jaw has a flexible medial section and rigid lateral sections, the medial section being proud of the lateral sections when the first jaw and the second jaw are in the open position, the medial section being electrically connected to a generator and a selective electrical contact electrically connecting the lateral sections to the medial section when the first jaw and the second jaw move to the closed position; closing the first jaw and the second jaw to grasp tissue therebetween; applying electrosurgical energy to coagulate tissue grasped between the first jaw and the second jaw; and pressing the first jaw and the second jaw together to cut the tissue.

Accordingly, pursuant to another aspect of the present invention, an end effector assembly of a forceps includes a first jaw with a tissue sealing surface and an electrode on the sealing surface and a second jaw with a tissue sealing surface and an electrode on the sealing surface, the first jaw and the second jaw being configured to move between an open position and a closed position, the sealing surface of at least one of the first jaw and the second jaw having a moveable distal section and a stationary proximal section. A portion of the moveable distal section is proud of the stationary proximal section when the first jaw and the second jaw are in the open position.

The foregoing aspect of the present invention can be further characterized by one or any combination of the features described herein, such as: the distal section translates relative to the proximal section; the sealing surfaces of both the first jaw and the second jaw have a flexible distal section and a rigid proximal section; the sealing surface of at least one of the first jaw and the second jaw has a pair of flexible distal sections; the sealing surfaces of both the first jaw and the second jaw have a pair of flexible distal sections; the end effector further includes a slot extending axially through a substantial portion of the first jaw and the second jaw and further comprising a blade that translates within the slot; at least one of the distal section and the proximal section has teeth for gripping tissue; the portion of the distal section is raised from the proximal section with at least one spring member; the electrodes are connected to a source of electrosurgical energy, the source generating electrosurgical energy to coagulate tissue grasped between the first jaw and the second jaw; the distal section and the proximal section are electrically connected, the electrode being on the distal section and the proximal section; and the moveable distal section is a rotatable distal section.

Accordingly, pursuant to another aspect of the present invention, an end effector assembly of a forceps includes a first jaw with a tissue sealing surface and an electrode on the sealing surface and a second jaw with a tissue sealing surface and an electrode on the sealing surface, the first jaw and the second jaw being configured to move between an open position and a closed position. The sealing surface of at least one of the first jaw and the second jaw has a moveable medial section and stationary lateral sections. The medial section rotates relative of the lateral sections. The axis of rotation can be parallel to the axial length of the first jaw and the second jaw.

Accordingly, pursuant to yet another aspect of the present invention, a method of using forceps includes one or more of the following steps: opening a first jaw and a second jaw of the forceps, the first jaw having a tissue sealing surface and an electrode on the sealing surface and the second jaw having a tissue sealing surface and an electrode on the sealing surface, the sealing surface of at least one of the first jaw and the second jaw has a flexible distal section and a rigid proximal section, the distal section either translating or rotating relative to the proximal section, at least a portion of the distal section being raised from the proximal section; closing the first jaw and the second jaw to grasp tissue therebetween; applying electrosurgical energy to coagulate tissue grasped between the first jaw and the second jaw; and pressing the first jaw and the second jaw together to cut the tissue.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, emphasis instead being placed upon illustrating the principles of the invention. In the drawings.

DETAILED DESCRIPTION

The following description is merely exemplary in nature and is not intended to limit the present disclosure, application, or uses.

Referring now to the drawings, a forceps, such as, for example, a laparoscopic forceps, embodying the principles of the present invention is illustrated therein and designated at 2. The forceps 2 may function to grip an object. The forceps 2 may be used during surgery to grip a feature of interest including: a part of a body, an anatomical feature, tissue, veins, arteries, or a combination thereof. The forceps 2 may function to be used in surgery, for example, laparoscopic surgery. The forceps 2 may be used with or without power. Current may be passed through the forceps 2 so that the forceps are used for electrosurgery. For example, a therapy current may be passed from one jaw to a second jaw when tissue is located within the jaw and the therapy current may coagulate blood, cauterize, cut, or a combination thereof. The forceps 2 may generally include one or more working assemblies and sufficient controls to work the one or more assemblies. The forceps 2 may include parts employed to perform the recited functions and may include generally, a stylet (e.g., a tubular member, a hollow tube, or an assembly of tubes), a hand piece, one or more operable mechanisms used to actuate the stylet, or a combination thereof. The hand piece may be an assembly of parts or housing structures capable of forming a hand piece structure with a cavity. Note that the present invention is not limited to laparoscopic procedures. That is, the below described jaws can be employed with any type of medical device that clamps onto tissue.

Figure 1:
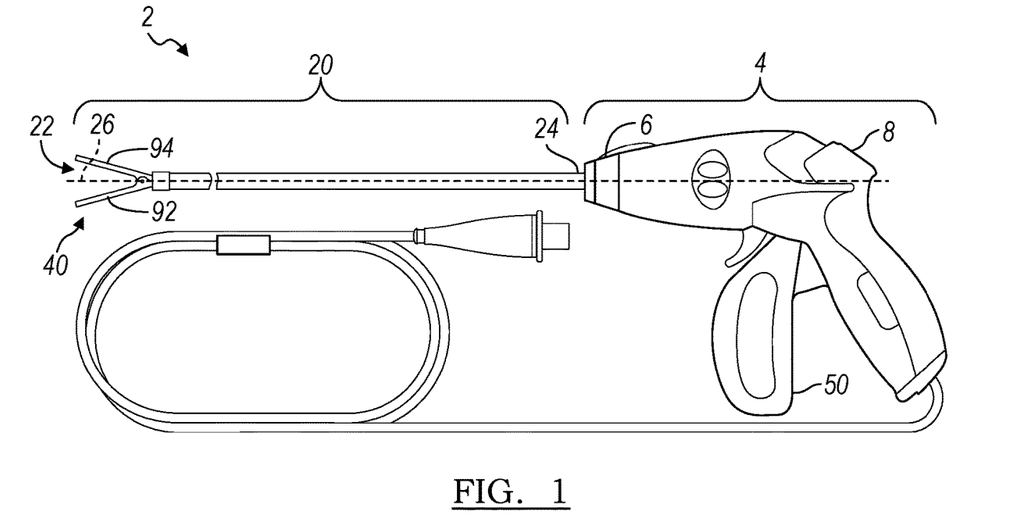
FIG. 1 illustrates an electrosurgical forceps in accordance with the principles of the present invention.
Figure 2:
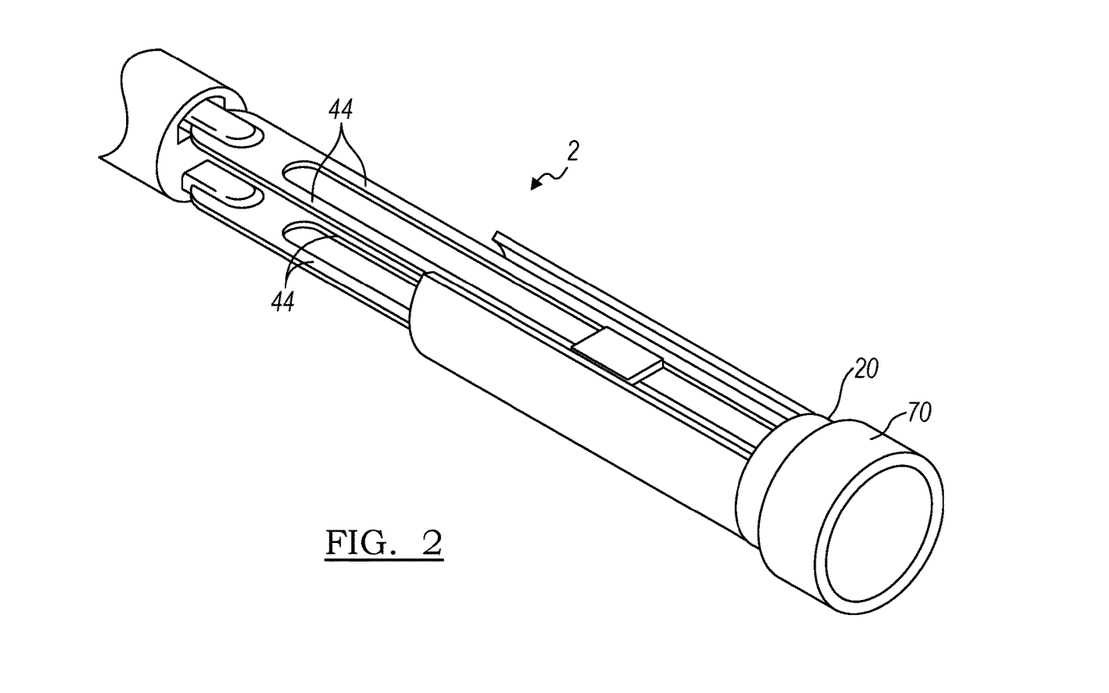
FIG. 2 an example of a set of jaws for the forceps shown in FIG. 1.

Turning now to FIG. 1, a side view of the forceps 2 is shown. The forceps 2 include a handpiece 4 having a distal end 6 and a proximal end 8. The handpiece 4 also includes at least one operable mechanism 50. A tubular member 20 has a proximal end 24 that is connected to the distal end 6 of the handpiece 4. The tubular member 20 includes a distal end 22 that includes jaws 40 extending therefrom. The jaws 40 have members 92 and 94 that open and close when the tubular member 20 is moved forward along the longitudinal axis 26 of the tubular member into contact with the members 92 and 94 or the jaws 40 are moved backwards along the longitudinal axis 26 into contact with the tubular member 20.

Figure 3:
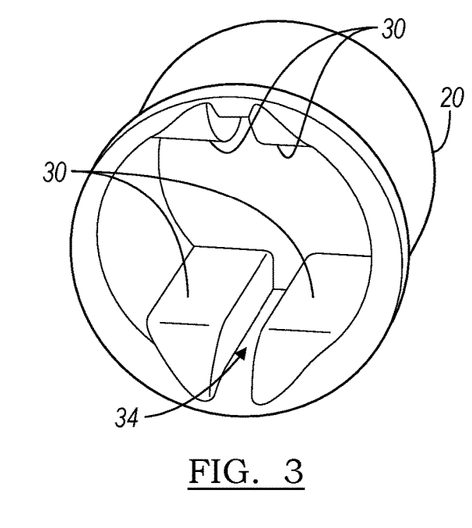
FIG. 3 illustrates an end of a tubular member and/or a camming shaft for the forceps.

Referring further to FIGS. 2 and 6 through 9, a camming shaft 70 is located on the forceps 2 with the jaws 40 extending therefrom. The members 92 and 94 are biased by the camming shaft 70 so that the jaws 40 are opened and closed. The members 92 and 94 include a medial portion or section 96 and 98, respectively, and a pair of slots 100 and 102 extend through the members 92 and 94, respectively. The member 92 includes a first compression surface 104 on lateral portions or sections of the member 92, that is, on both sides of the medial section 96, and the medial section 96 includes a second compression surface 108 on both sides of the slot 100. The member 94 includes a first compression surface 106 on a lateral portion or section of the member 94, that is, on both sides of the medial section 98, and the medial section 98 includes a second compression surface 110 both sides of the slot 102, FIG. 3 illustrates the end of the tubular member 20 or a camming shaft showing a pair of internal flat portions 30 along the top surfaces and the bottom surfaces. A blade recess 34 extends between the pair of internal flat portions 30 so that a blade 400 (FIGS. 12 and 13) extends out of the tubular member 20.

Figure 4:
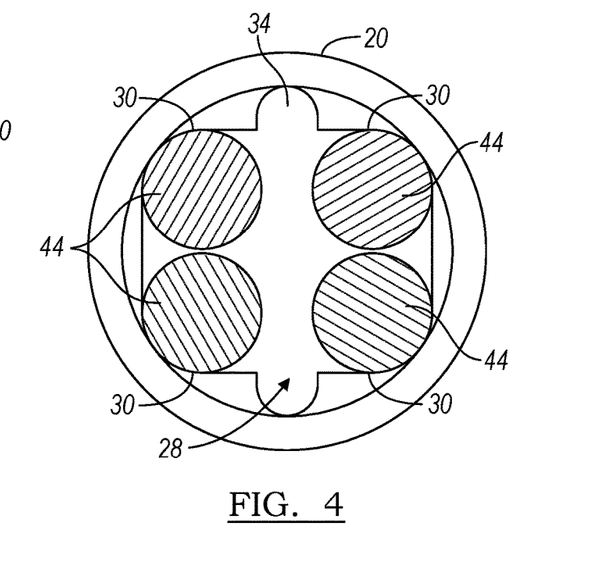
FIG. 4 illustrates an end view of a tubular member and/or a camming shaft.

FIG. 4 illustrates a cross-sectional view of a tubular member 20. The internal flat portions 30 include at least a portion that has a complementary shape to that of the legs of the jaws 44. Accordingly, as the tubular member 20 or the legs 44 axially move, the internal flat portions 30 control the orientation and movement of the jaws.

Figure 5:
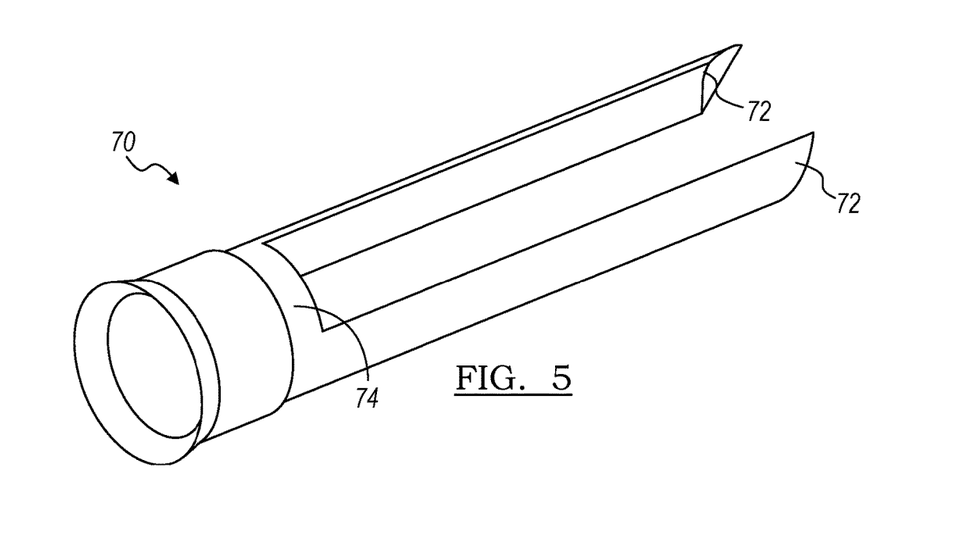
FIG. 5 illustrates a perspective view of a camming shaft.

FIG. 5 illustrates a perspective view of one example of a camming shaft 70 that is inserted into the tubular member 20. The camming shaft 70 includes a molded flare 74 with a pair of protrusions 72 extending therefrom.

Figure 6:
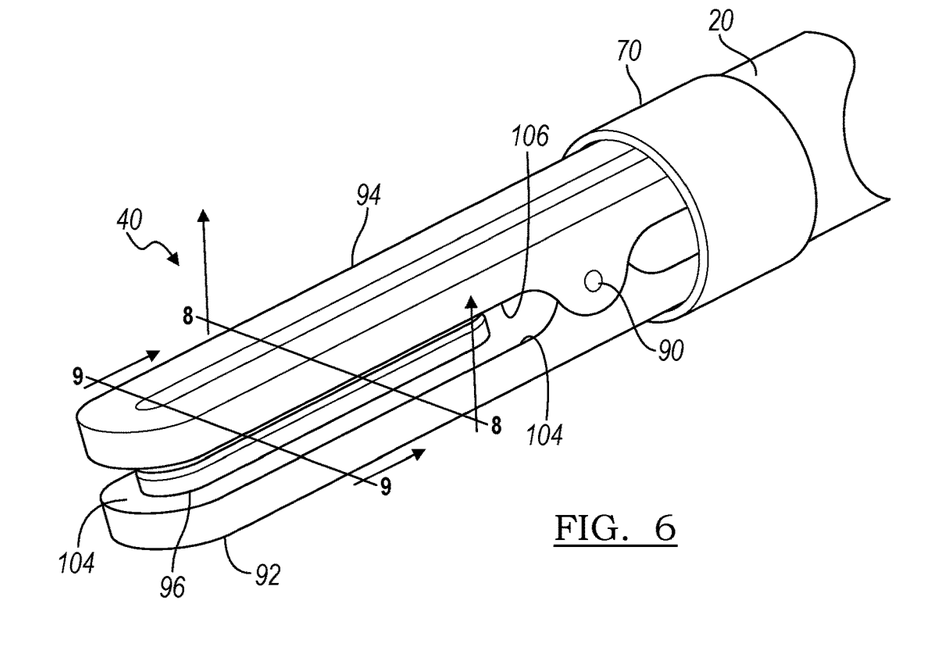
FIG. 6 illustrates a perspective view of the forceps shown in FIG. 1.
Figure 7:
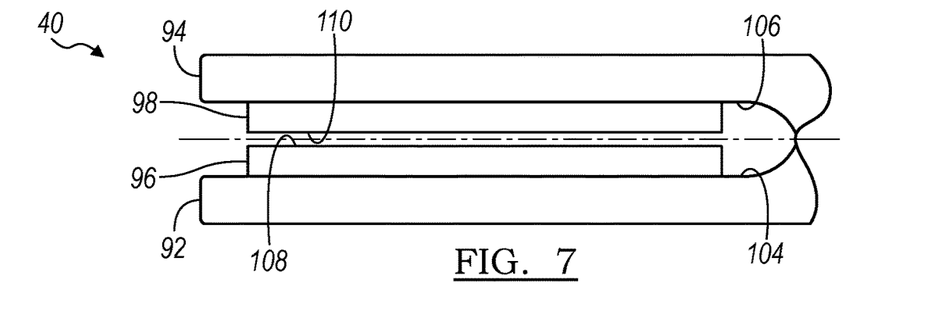
FIG. 7 illustrates a side view of the jaws.
Figure 8:
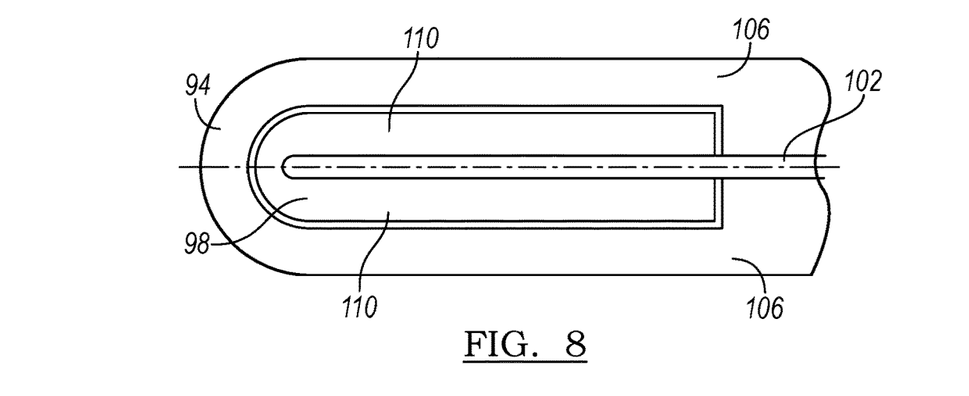
FIG. 8 illustrates two sections of the upper jaw.

FIG. 6 illustrates the jaws 40 including a pin 90 located between the jaws. The pin 90 holds the jaw members 92 and 94 together and provide a pivot point for the jaw members 92 and 94 such that the members 92 and 94 close when the tubular member 20 is slid over the opposing members 92 and 94.

Turning back to FIG. 9, the jaw members 92 and 94 are shown clamping and sealing a vessel, V. The jaw members 92 and 94 form a first compression zone with the compression surfaces 104 and 106 and a second compression zone with the compression surfaces 108 and 110 when the jaw members 92 and 94 are clamped together. In certain arrangements, a set of biasing members 112A, 112B, 112C and 112D are disposed between the medial sections 96 and 98 and respective upper body portions 116 and 118 of the jaw members 92 and 94, so that the medial sections 96 and 98 are able to translate relative to the body portions 116 and 118, as indicated by the arrows 114 (that is, in a direction perpendicular to the sealing surfaces). As such, when the jaw members 92 and 94 are open, the medial sections 96 and 98, and hence, the second compression surfaces 108 and 110, are proud of the first compression surfaces 104 and 106; that is, the second compression surfaces 108 and 110 extend inwardly away from the first compression surfaces 104 and 106. The biasing members 112A, 1126, 112C and 112D can be made of any suitable spring-like material, such as, for example, elastic materials. The biasing members 112A, 112B, 112C and 112D can be coiled springs or solid compression members. Accordingly, the jaws 40 is a two-stage end-effector with the first compression zones produced by the compression surfaces 104 and 106 being more rigid than the flexible second compression zones produced by the compression surfaces 108 and 110. Note that the two compression zones can extend along a portion of or all of the jaw members 92 and 94.

Figure 9:
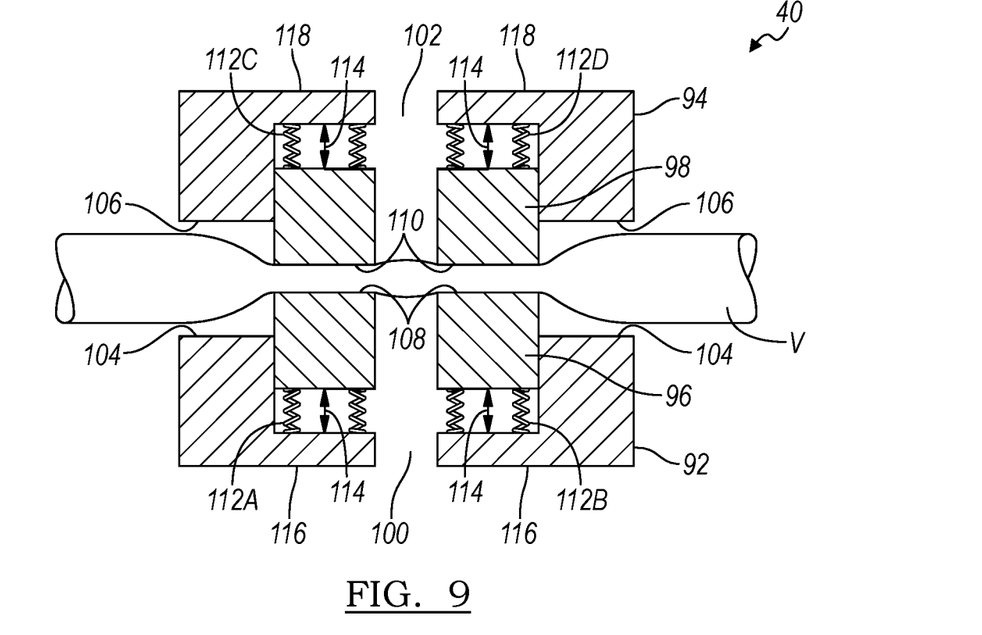
FIG. 9 illustrates a cross-sectional view of the jaws sealing a vessel.

Accordingly, as the jaw members 92 and 94 clamped onto a smaller vessel, V, only the medial second compression zones formed by the compression surfaces 108 and 110 clamp and close on the vessel, V. Whereas, with a larger vessel, V, both the lateral first compression zones formed by the compression surfaces 104 and 106 and the second compression zones formed by the compression surfaces 108 and 110 clamp and close on the vessel, V, such that the lateral first compression zones produce a lower compression force on the vessel, V, than the medial second compression zones. In various arrangements, the medial sections 108 and 110 and/or the body portions 116 and 118 can be electrical connected to a generator that provides a source of electrosurgical energy so that a RF voltage with different potentials can be applied to the electrically connected sections of the jaw members 92 and 94. The RF voltage produces a current that passes from one jaw member to the other jaw member electrode through tissue, thereby heating the tissue to coagulate or cut the tissue.

Figure 10:
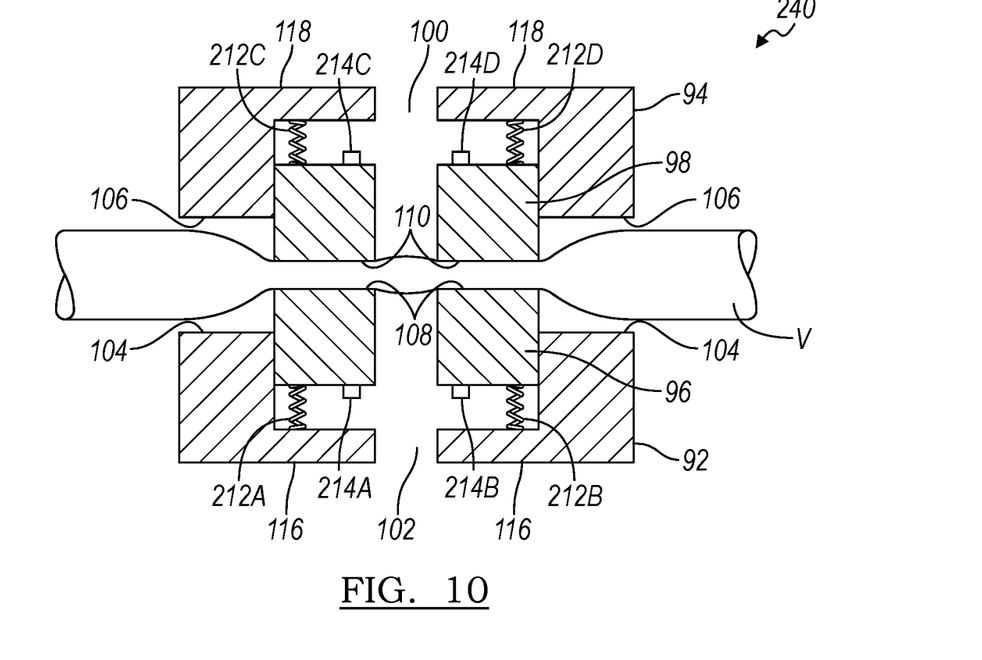
FIG. 10 illustrates a cross-sectional view of another set of jaws sealing a vessel in accordance with the principles of the present invention.

Turning now to FIG. 10, there is shown an alternative set of jaws 240 in accordance with the principles of the present invention. The jaws 240 are similar to the previously described jaws 40. The jaws 240, however, have a set of electrical contacts 214A, 214B, 214C and 214D in addition to a set of biasing members 212A, 212B, 212C and 212D disposed between the medial sections 96 and 98 and respective upper body portions 116 and 118 of the jaw members 92 and 94. The biasing members 212A, 212B, 212C and 212D can be made of any suitable spring-like material, such as, for example, elastic materials. The biasing members 212A, 212B, 212C and 212D can be coiled springs or solid compression members. Hence, again, the first compression zones produced by the compression surfaces 104 and 106 are more rigid than the flexible second compression zones produced by the compression surfaces 108 and 110. The electrical contacts 214A, 214B, 214C and 214D electrically connect the medial sections with the body portions 116 and 118 when the jaw members 92 and 94 are clamped onto the vessel, V with a desired amount of force. Hence, if the medial sections 96 and 98 are electrically connected to a generator that provides a source of electrosurgical energy, a current passes from both the lateral and medial sections of one jaw member to the lateral and medial sections of the other jaw member through tissue clamped by the jaw members 92 and 94, thereby heating the tissue to coagulate or cut the tissue when the jaw members are closed with a desired amount of force.

Figure 11:
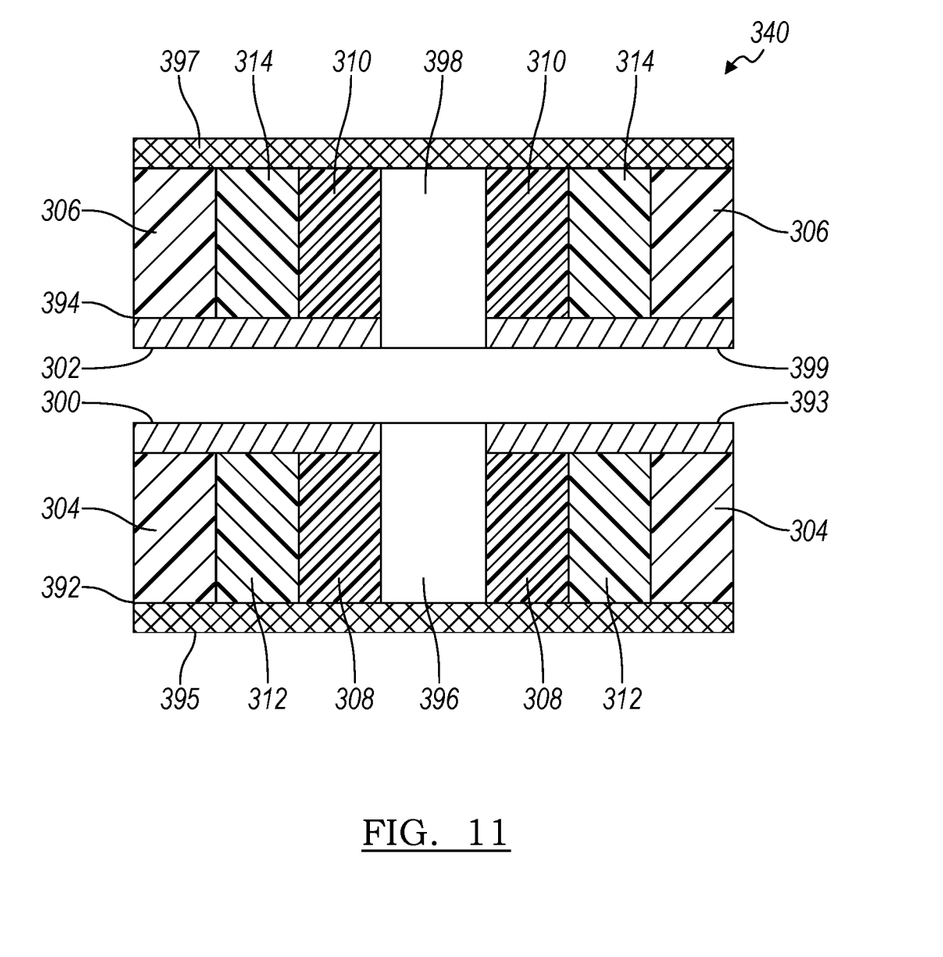
FIG. 11 illustrates a cross-sectional view of yet another set of jaws in accordance with the principles of the present invention.

FIG. 11 illustrates yet another alternative set of jaws 340 in accordance with the principles of the present invention.

The jaws 340 include a first jaw member 392 and a second jaw member 394. The first jaw member 392 includes a jaw body or support member 395 and a sealing plate 393 disposed on both sides of a slot 396. The exterior surface of the sealing plate 393 defines a sealing surface 300. A layer of pliable material 304, 308, 312 is disposed between the jaw body 395 and the sealing plate 393. The layer of pliable mater is made of separate cells placed side by side with different thickness, the medial or center cells 308 being more flexible than the lateral cells 304. In certain arrangements, the layer of pliable material includes the medial cells 308 positioned adjacent to the lateral cells 304, while in other arrangements intermediate cells 312 are positioned between the medial cells 308 and the lateral cells 304 to provide an additional transition from the more flexible medial cells 308 to the stiffer lateral cells 304.

The second jaw member 394 includes a jaw body 397 and a sealing plate 399 disposed on both sides of a slot 398. The exterior surface of the sealing plate 399 defines a sealing surface 302. A layer of pliable material 306, 310, 314 is disposed between the jaw body 397 and the sealing plate 399. The layer of pliable mater is made of separate cells placed side by side with different thickness, the medial or center cells 310 being more flexible than the lateral cells 304. In certain arrangements, the layer of pliable material includes the medial cells 310 positioned adjacent to the lateral cells 306, while in other arrangements intermediate cells 314 are positioned between the medial cells 310 and the lateral cells 306 to provide an additional transition from the more flexible medial cells 310 to the stiffer lateral cells 306. The layers of pliable material 304, 308, 312 and 306, 310, 314 can extend along a portion of or all of the jaw members 392 and 394.

Accordingly, the sealing surfaces 300 and 302 above the lateral cells 304 and 306 form a first compression zone and the sealing surfaces above the medial cells 308 and 310 form a second compression zone when the jaw members 392 and 394 are clamped together on a vessel, the first compression zone being less flexible than the second compression zone. Again, if the jaw members 392 and 394 include the intermediate cells 312 and 314, the stiffness of the cells 312 and 314 can be selected to provide a desired transition from the first compression zone to the second compression zone.

The cells 304, 306, 308, 310, 312, 314 can be made from any suitable pliable materials such as elastomers. In some arrangements, none of the cells 304, 306, 308, 310, 312, 314 are electrically conductive. In other arrangements, some or all of the cells 304, 306, 308, 310, 312, 314 can be electrically conductive. Hence, when the jaw members 392 and 394 are connected to a generator that provides a source of electrical energy, a voltage with different potentials can be applied to the electrically conductive cells such that a current passes from one jaw member to the other jaw member through tissue clamped between the jaw members to coagulate or cut the tissue.

Figure 12:
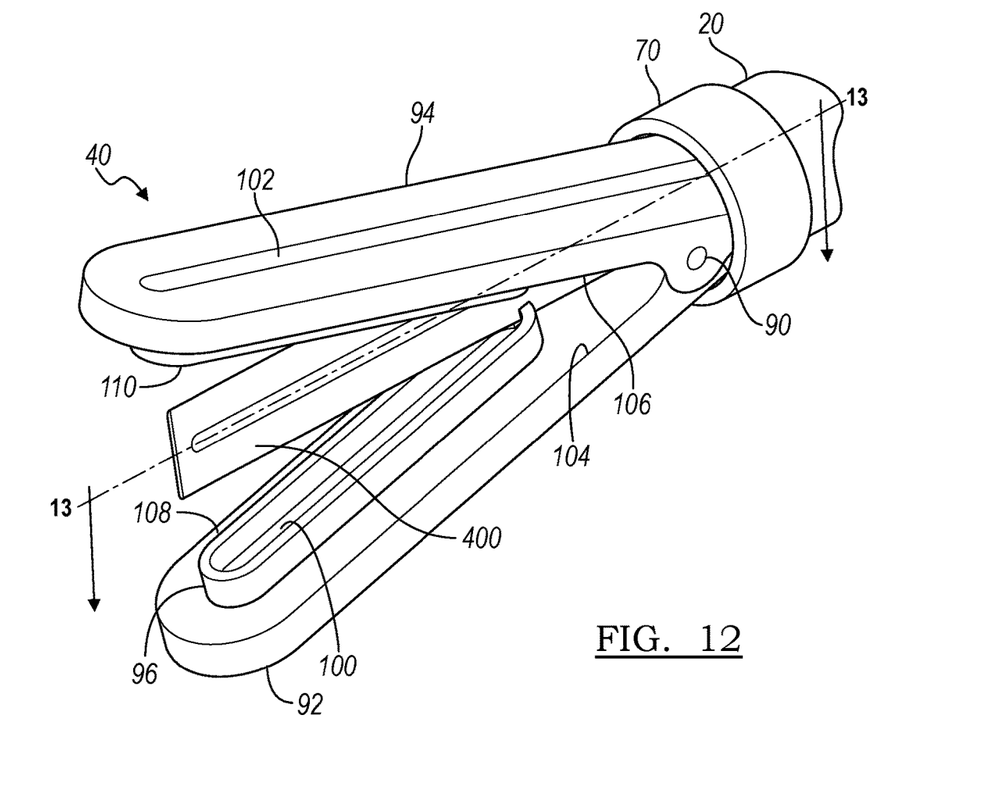
FIG. 12 illustrates a perspective view of the jaws shown in FIG. 6 with a cutting blade.
Figure 13:
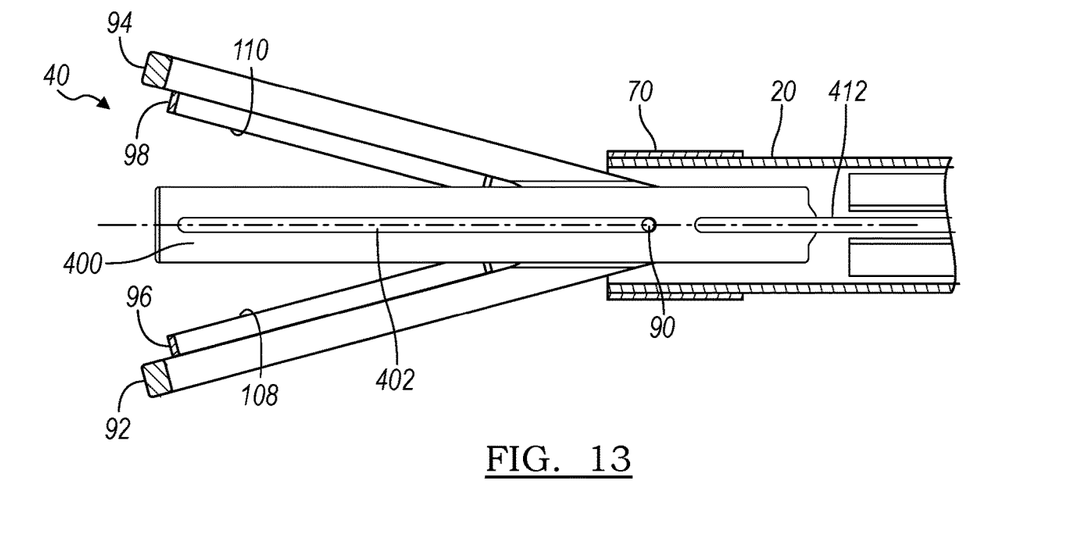
FIG. 13 illustrates a side view of the jaws shown in FIG. 6 with the cutting blade.

Any of the jaw arrangements 40, 240 and 340 described previously can include a cutting blade. For example, as shown in FIGS. 12 and 13, the jaws 40 are shown with a blade 400. The blade 400 includes a slot 402 that engages with the pin 90 to allow the blade 400 to reciprocate along the pin 90. The blade 400 is connected to a blade shaft 412. Hence, axial movement of the blade shaft 412 results in reciprocating axial movement of the blade 400 along the slots 100 and 102 of the jaw members 92 and 94 to cut tissue clamped between the jaw members 92 and 94. A similar blade arrangement can be added to the jaws 240 and 340.

Figure 14A:
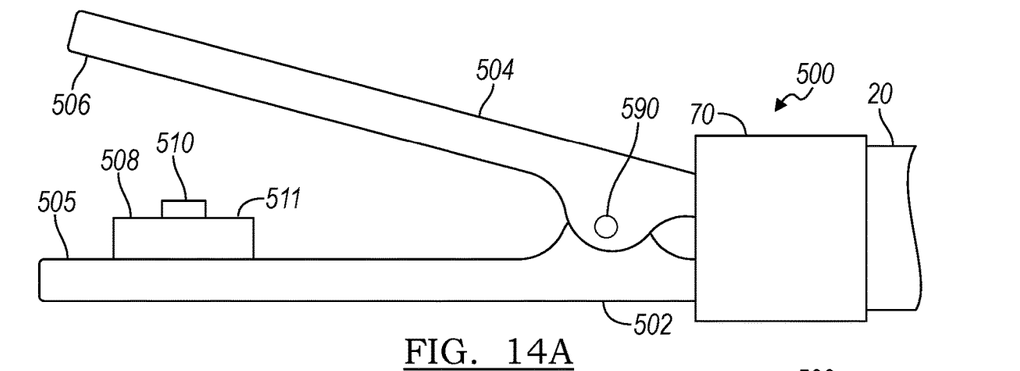
FIG. 14A illustrates a side view of yet another set of jaws in accordance with the principles of the present invention.
Figure 14B:
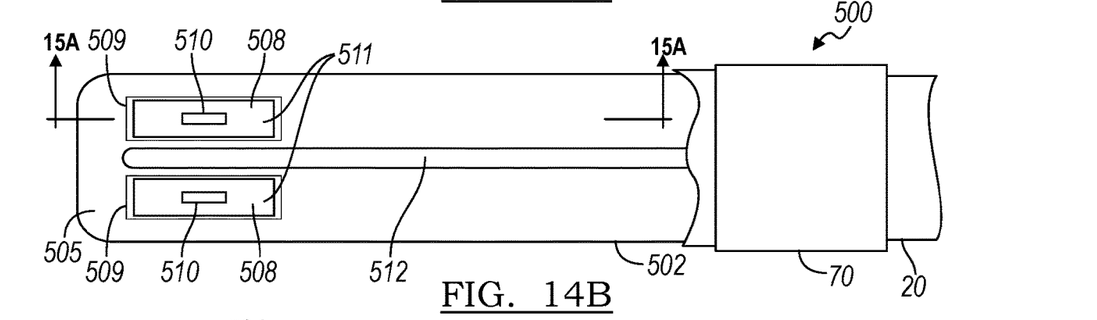
FIG. 14B illustrates a top view of the bottom jaw shown in FIG. 14A.
Figure 16:
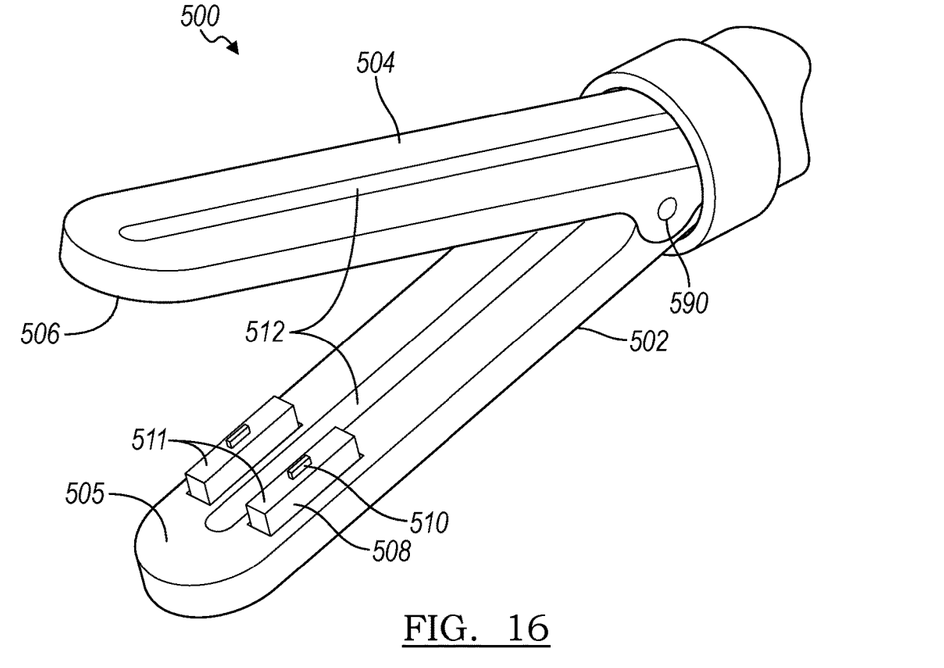
FIG. 16 illustrates a perspective view of the set of jaws shown in FIG. 14A.

Turning now to FIGS. 14A and 14B, there is shown an alternative set of jaws 500 in accordance with the principles of the present invention. The set of jaws 500 includes a first jaw member 502 and a second jaw member 504. The set of jaws 500 includes a pin 590 located between the jaws. The pin 590 holds the jaw members 502 and 504 together and provides a pivot point for the jaw members 502 and 504 such that the members 502 and 504 close when the tubular member 20 is slid over the opposing members 502 and 504. In some arrangements, the jaw members 502 and 504 include blade slots 512 (FIG. 16) to accommodate the blade arrangement described above and shown above in FIGS. 12 and 13.

The exterior surface of the first jaw member 502 defines a sealing surface 505. The first jaw member 502 also includes one or two retainers 508 with an exterior surface that defines a second sealing surface 511. The second jaw member 504 has an exterior surface that defines a sealing surface 506.

Figure 15A:
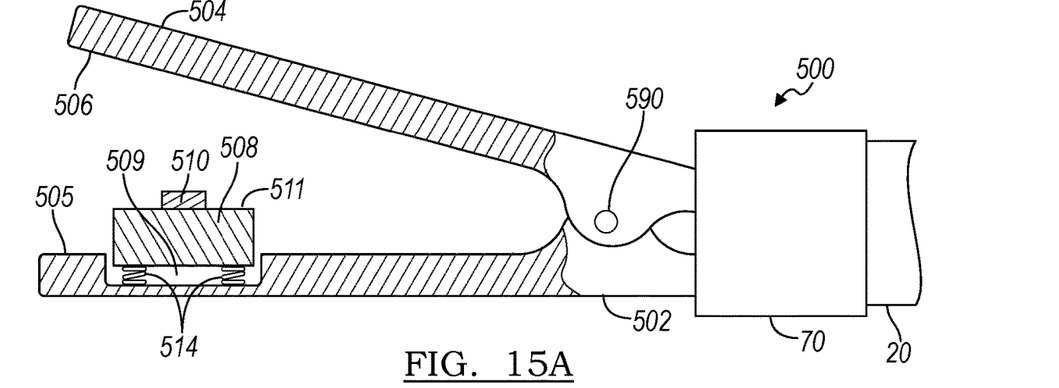
FIG. 15A illustrates a cross-sectional view of the jaws taken along the line 15A-15A of FIG. 14B when the jaws are in an open position.
Figure 15B:
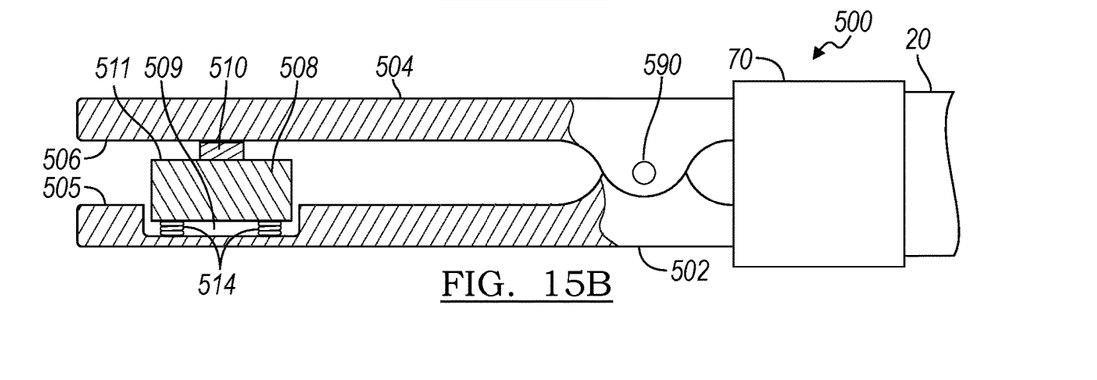
FIG. 15B illustrates a cross-sectional view of the jaws taken along the line 15A-15A of FIG. 14B when the jaws are in a closed position.

As shown in FIGS. 15A and 15B, the retainers 508 are positioned in respective openings 509 in the first jaw member 502. In certain arrangements, one or more biasing members 514 are disposed between each retainer 508 and the first jaw member 502. As such, when the jaw members 502 and 504 are open, the retainer 508, and hence, the second sealing surfaces 511, are proud of the sealing surface 505. The biasing members 514 can be made of any suitable spring-like material, such as, for example, elastic materials. The biasing members 514 can be coiled springs or solid compression members. Accordingly, the retainers 508 are movable relative to the first jaw member such that the set of jaws 500 is a two-stage end-effector with the first compression zones produced by the sealing surfaces 505 and 506 being more rigid than flexible second compression zones produced by the sealing surfaces 506 and 511 when the jaws members 502 and 504 are moved from the open position (FIG. 15A) to the closed position (FIG. 15B).

In various arrangements, the retainers 508 are electrically connected to the first jaw member 502 such that both the retainers 508 and the first jaw member 502 are electrically conductive. In other arrangements, either the retainers 508 or the jaw member 502 are electrically conductive. All or a portion of the second jaw member 504 can be electrically conductive as well. Accordingly, the jaws 500 can be electrical connected to a generator that provides a source of electrosurgical energy so that a RF voltage with different potentials can be applied to the electrically connected sections of the jaw members 502 and 504 in a bipolar jaw arrangement. The RF voltage produces a current that passes from one jaw member to the other jaw member electrode through tissue, thereby heating the tissue to coagulate or cut the tissue. The retainers 508 can include one or more non-conductive stop 510 positioned between the sealing surfaces 511 and the sealing surface 506 to prevent shorting the electrically portions of the jaw members 502 and 504.

Figure 17:
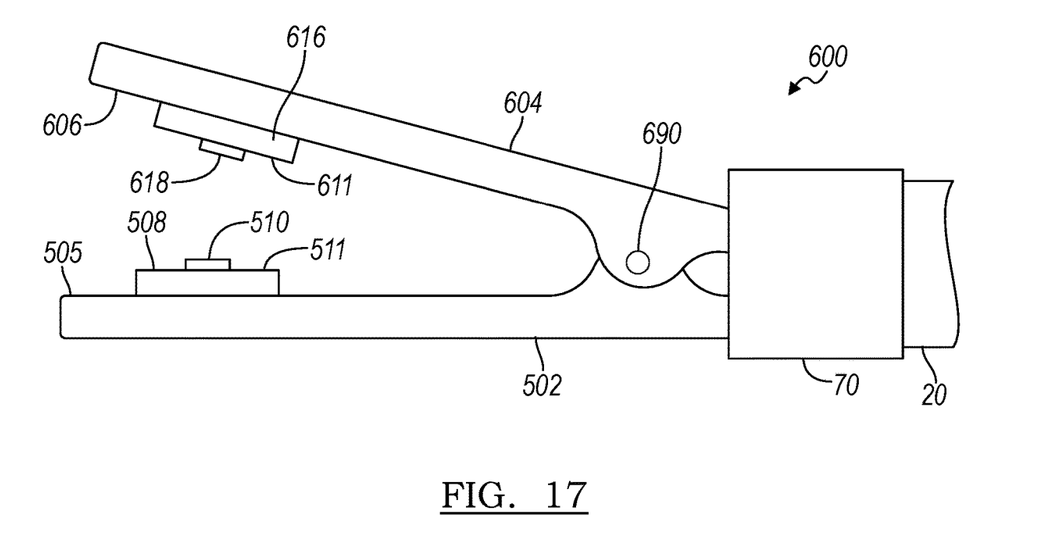
FIG. 17 illustrates a side view of yet another set of jaws in accordance with the principles of the present invention.

Turning now to FIG. 17, there is shown yet another set of jaws 600 in accordance with the principles of the present invention. The set of jaws 600 includes the first jaw member 502 described above and a second jaw member 604. The set of jaws 600 includes a pin 690 located between the jaws. The pin 690 holds the jaw members 502 and 604 together and provides a pivot point for the jaw members 502 and 604 such that the members 502 and 604 close when the tubular member 20 is slid over the opposing members 502 and 604. In some arrangements, the jaw members 502 and 604 include blade slots similar to the blade slots 512 shown in FIG. 16 to accommodate the blade arrangement described above and shown above in FIGS. 12 and 13.

The exterior surface of the second jaw member 604 defines a sealing surface 606. The second jaw member 604 also includes one or two retainers 616 with an exterior surface that defines a second sealing surface 611. Again, the arrangement for the first jaw member 502 is the same as described previously with respect to the jaws 500.

Figure 18A:
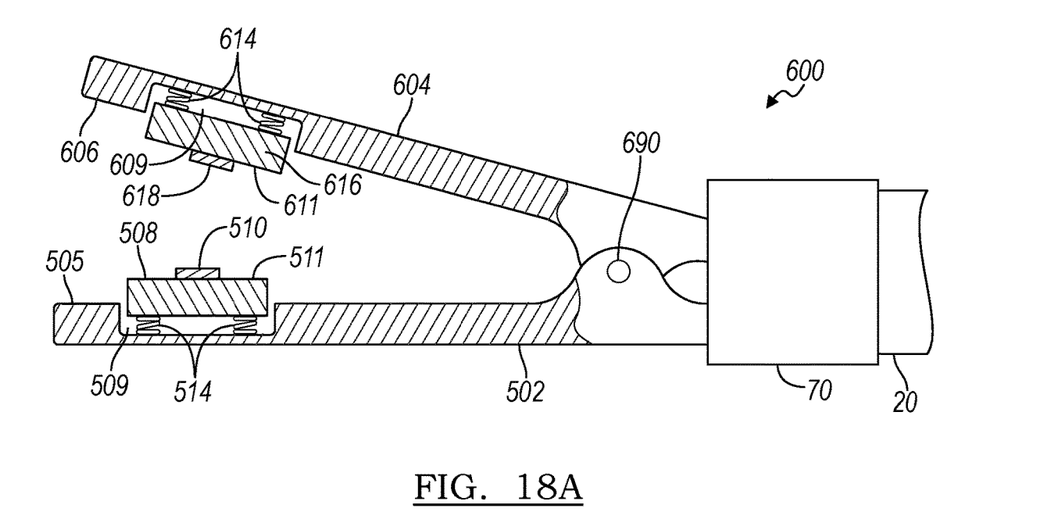
FIG. 18A illustrates a cross-sectional view of the jaws shown in FIG. 17A when the jaws are in an open position.
Figure 18B:
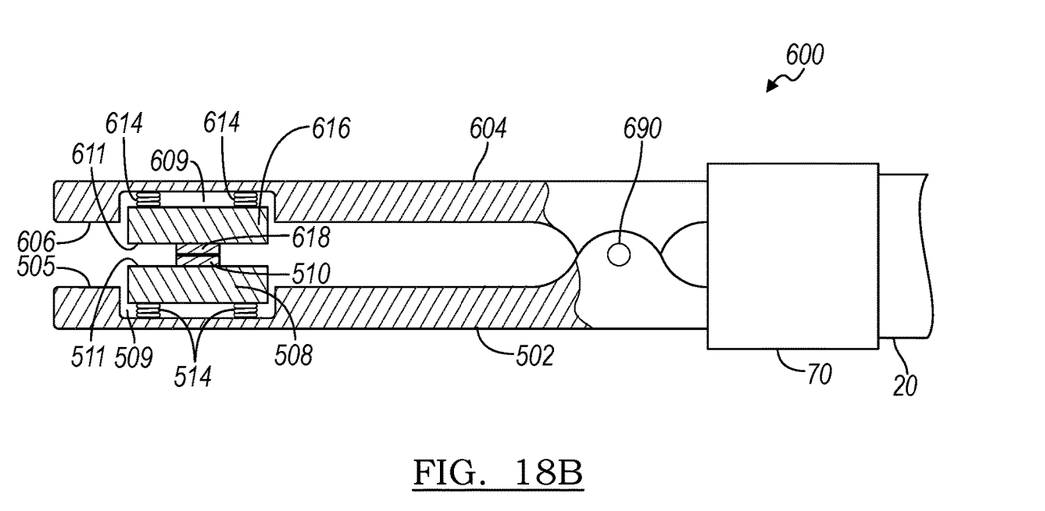
FIG. 18B illustrates a cross-sectional view of the jaws shown in FIG. 17A when the jaws are in a closed position.

As shown in FIGS. 18A and 18B, the retainers 616 are positioned in respective openings 609 in the second jaw member 604. In certain arrangements, one or more biasing members 614 are disposed between each retainer 516 and the second jaw member 604. As such, when the jaw members 502 and 604 are open, the retainers 508, and hence, the second sealing surfaces 511, are proud of the sealing surface 505, and the retainers 616, and hence the second sealing surfaces 611 are proud of the sealing surface 606. The biasing members 614 can be made of any suitable spring-like material, such as, for example, elastic materials. The biasing members 614 can be coiled springs or solid compression members. Accordingly, the retainers 508 are movable relative to the first jaw member 502 and the retainers 616 are moveable relative to the second jaw member 604 so that the set of jaws 600 is a two-stage end-effector with the first compression zones produced by the sealing surfaces 505 and 606 being more rigid than flexible second compression zones produced by the sealing surfaces 511 and 611 when the jaws members 502 and 604 are moved from the open position (FIG. 18A) to the closed position (FIG. 18B).

In various arrangements, the retainers 508 are electrically connected to the first jaw member 502 such that both the retainers 508 and the first jaw member 502 are electrically conductive. In other arrangements, either the retainers 508 or the jaw member 502 are electrically conductive. Similarly, in some arrangements the retainers 616 are electrically connected to the second jaw member 604 such that both the retainers 616 and the second jaw member 604 are electrically conductive, while in arrangements, either the retainers 616 or the jaw member 604 are electrically conductive. Accordingly, the jaws 600 can be electrical connected to a generator that provides a source of electrosurgical energy so that a RF voltage with different potentials can be applied to the electrically connected sections of the jaw members 502 and 604 in a bipolar jaw arrangement. The RF voltage produces a current that passes from one jaw member to the other jaw member electrode through tissue, thereby heating the tissue to coagulate or cut the tissue. The retainers 508 and 616 can include one or more non-conductive stop 510 and 618 positioned between the sealing surfaces 511 and the sealing surfaces 611 to prevent shorting the electrically portions of the jaw members 502 and 604.

Figure 19A:
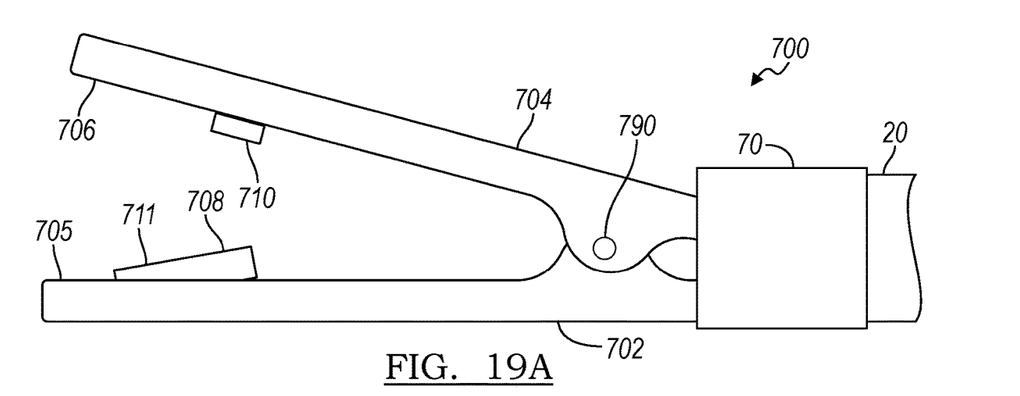
FIG. 19A illustrates a side view of yet another set of jaws in accordance with the principles of the present invention.
Figure 19B:
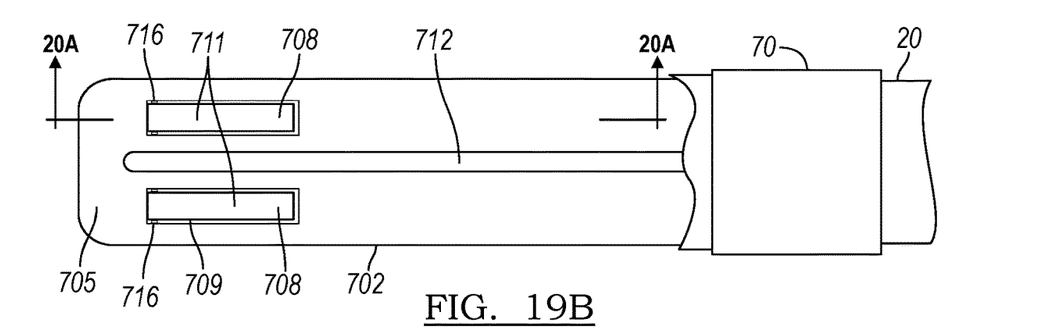
FIG. 19B illustrates a top view of the bottom jaw shown in FIG. 19A.

Referring now to FIGS. 19A and 19B, there is shown an alternative set of jaws 700 in accordance with the principles of the present invention. The set of jaws 700 includes a first jaw member 702 and a second jaw member 704. The set of jaws 700 includes a pin 790 located between the jaws. The pin 790 holds the jaw members 702 and 704 together and provides a pivot point for the jaw members 702 and 704 such that the members 702 and 704 close when the tubular member 20 is slid over the opposing members 702 and 704. In some arrangements, the jaw members 702 and 704 include blade slots similar to the blade slots 512 shown in FIG. 16 to accommodate the blade arrangement described above and shown above in FIGS. 12 and 13.

The exterior surface of the first jaw member 702 defines a sealing surface 705. The first jaw member 702 also includes one or two retainers 708 with an exterior surface that defines a second sealing surface 711. The second jaw member 704 has an exterior surface that defines a sealing surface 706.

Figure 20A:
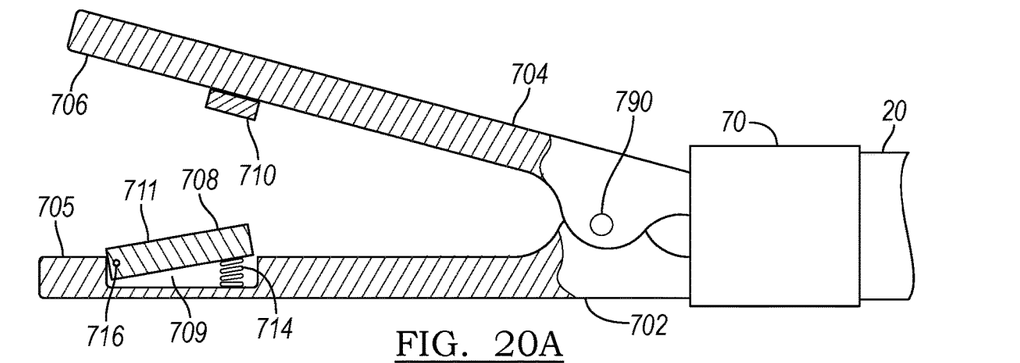
FIG. 20A illustrates a cross-sectional view of the jaws shown in FIG. 19A when the jaws are in an open position.
Figure 20B:
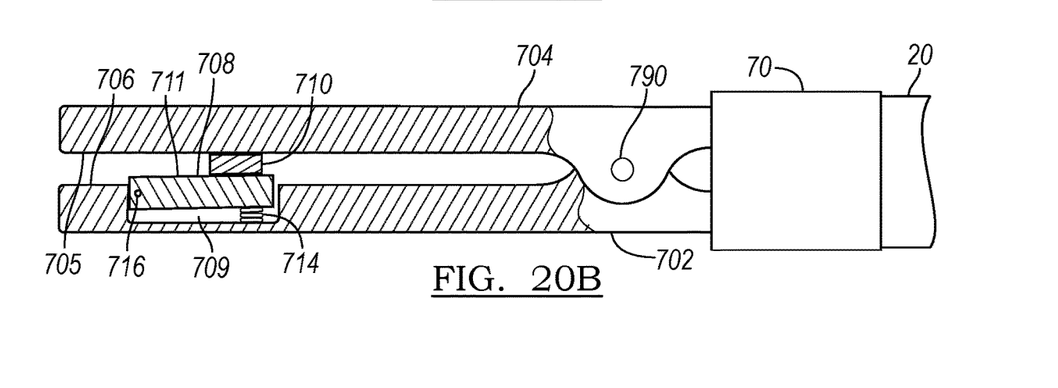
FIG. 20B illustrates a cross-sectional view of the jaws shown in FIG. 19A when the jaws are in a closed position.

As shown in FIGS. 20A and 20B, the retainers 708 are positioned in respective openings 709 in the first jaw member 702. The retainers 708 are attached to first jaw member 702 with pins 716 that provide a pivot point for the retainers 708 with respect to the first jaw member 702. In certain arrangements, one or more biasing members 714 are disposed between each retainer 708 and the first jaw member 702. As such, when the jaw members 702 and 704 are open, the retainers 708 pivot about the pins 716 outwardly from the sealing surface 705 such that a portion of the retainer 708, and hence, a portion of the second sealing surfaces 711, are proud of the sealing surface 705. The biasing members 714 can be made of any suitable spring-like material, such as, for example, elastic materials. The biasing members 714 can be coiled springs or solid compression members. Accordingly, the retainers 708 are movable relative to the first jaw member such that the set of jaws 700 is a two-stage end-effector with the first compression zones produced by the sealing surfaces 505 and 506 being more rigid than flexible second compression zones produced by the sealing surfaces 706 and 711 when the jaws members 702 and 704 are moved from the open position (FIG. 20A) to the closed position (FIG. 20B).

In various arrangements, the retainers 708 are electrically connected to the first jaw member 702 such that both the retainers 708 and the first jaw member 702 are electrically conductive. In other arrangements, either the retainers 708 or the jaw member 702 are electrically conductive. All or a portion of the second jaw member 704 can be electrically conductive as well. Accordingly, the jaws 700 can be electrical connected to a generator that provides a source of electrosurgical energy so that a RF voltage with different potentials can be applied to the electrically connected sections of the jaw members 702 and 704 in a bipolar jaw arrangement. The RF voltage produces a current that passes from one jaw member to the other jaw member electrode through tissue, thereby heating the tissue to coagulate or cut the tissue. The jaw member 704 can include one or more non-conductive stop 710 positioned between the sealing surfaces 711 and the sealing surface 706 to prevent shorting the electrically portions of the jaw members 702 and 704.

Although the previously described jaws were directed to one jaw member pivotally attached to another jaw member, the present invention contemplates any type of jaw member that clamps onto tissue with another jaw member. For example, the jaw members can clamp onto tissue as the jaw members move toward each other in any suitable manner including translational and rotational movement; that is, the distal section can rotate or translate relative to the proximal section. Further, as mentioned previously, various components of the any of the above-described jaw members can be electrically conductive. The components themselves can be electrically conductive electrodes or electrically conductive material can be added to the component to form an electrode on the component. Any of the above described jaw members can have teeth for gripping tissue.

The description of the invention is merely exemplary in nature and variations that do not depart from the gist of the invention are intended to be within the scope of the invention. Such variations are not to be regarded as a departure from the spirit and scope of the invention.

What is claimed is:

1. A forceps comprising:
   an end effector assembly comprising:

a first jaw including:
  an upper body defining an upper compression surface; and
  an upper medial section having an upper tissue sealing surface that extends below the upper compression surface, the upper medial section movable relative to the upper body; and
a second jaw movable together with the first jaw between an open position and a closed position, the second jaw including:
  a lower body defining a lower compression surface;
  a lower medial section having a lower tissue sealing surface that extends above the lower compression surface, the lower medial section movable relative to the lower body, wherein the upper body, the lower body, the upper medial section, and the lower medial section together define a blade slot to receive an axial blade therein,
  wherein the tissue sealing surface of at least one of the first jaw and the second jaw has a distal section and a proximal section that form separate compression zones.

2. The forceps of claim 1, wherein a first compression zone formed by the distal section has a different rigidity compared to a second compression zone formed by the proximal section.

3. The forceps of claim 2, wherein the first compression zone produces a first compression force that is different compared to a second compression force formed by the second compression zone.

4. The forceps of claim 1, wherein the distal section is configured to move relative to the proximal section.

5. The forceps of claim 1, wherein the upper tissue sealing surface of the first jaw includes a first electrode and the lower tissue sealing surface of the second jaw includes a second electrode.

6. The forceps of claim 1, wherein the sealing surface of at least one of the first jaw and the second jaw has a pair of distal sections.

7. The forceps of claim 1, wherein the sealing surfaces of both the first jaw and the second jaw have a pair of distal sections.

8. The forceps of claim 1, further comprising:
a blade that is translatable within the blade slot.

9. The forceps of claim 1, wherein at least one of the distal section and the proximal section has teeth for gripping tissue.

10. The forceps of claim 1, wherein the tissue sealing surfaces of the first and second jaw include electrodes that are connected to a source of electrosurgical energy, the source generating electrosurgical energy to coagulate tissue grasped between the first jaw and the second jaw, and wherein the distal section and the proximal section are electrically connected, the electrodes being on the distal section and the proximal section.

11. The forceps of claim 1, wherein the distal section is configured to at least one of translate or rotate relative to the proximal section.

12. A forceps comprising:
an end effector assembly comprising:
  a first jaw including:
    a first body defining an upper compression surface; and
    a first medial portion having a first tissue sealing surface that extends below the upper compression surface and an electrode on the first tissue sealing surface, the first medial portion movable relative to the first body; and
  a second jaw including:
    a second body defining a lower compression surface;
    a second medial portion having a second tissue sealing surface that extends above the lower compression surface and an electrode on the second tissue sealing surface, wherein the first body, the first medial portion, the second body, and the second medial portion define a blade slot configured to receive a reciprocating blade therein,
    wherein the first jaw and the second jaw move between an open position and a closed position,
    wherein the sealing surface of at least one of the first jaw and the second jaw has at least two compression sections extending along a longitudinal direction of the sealing surface such that a first compression section of the at least two compression sections is positioned proximal to a second compression section of the at least two compression sections, and
    wherein the first compression section is moveable relative to the second compression section.

13. The forceps of claim 12, wherein a first compression zone formed by the first compression section has a different rigidity compared to a second compression zone formed by the second compression section.

14. The forceps of claim 12, wherein a first compression zone is provided by the first compression section and a second compression zone is provided by the second compression section, and wherein the first compression zone and the second compression zone are each configured to apply a separate compression force to tissue grasped between the first and second jaw.

15. The forceps of claim 14, wherein the first compression zone produces a first compression force and the second compression zone produces a second compression force, wherein the first compression force is different from the second compression force.

16. The forceps of claim 12, comprising:
a blade that is translatable within the blade slot.

17. The forceps of claim 12, wherein the second compression section is configured to at least one of translate or rotate relative to the first compression section.

* * * * *